(12) United States Patent
Zhang et al.

(10) Patent No.: US 12,376,584 B2
(45) Date of Patent: Aug. 5, 2025

(54) IN-VITRO CULTURE, INDUCTION, ACTIVATION AND CRYOPRESERVATION METHOD AND CELL BANK ESTABLISHMENT FOR IMMUNE CELLS

(71) Applicant: Qingdao Restore Biotechnology Co., Ltd., Qingdao (CN)

(72) Inventors: Bingqiang Zhang, Qingdao (CN); Mengmeng Chen, Qingdao (CN)

(*) Notice: Subject to any disclaimer, the term of this patent is extended or adjusted under 35 U.S.C. 154(b) by 375 days.

(21) Appl. No.: 17/634,556

(22) PCT Filed: May 26, 2020

(86) PCT No.: PCT/CN2020/092287
§ 371 (c)(1),
(2) Date: Feb. 11, 2022

(87) PCT Pub. No.: WO2021/223274
PCT Pub. Date: Nov. 11, 2021

(65) Prior Publication Data
US 2023/0051425 A1    Feb. 16, 2023

(30) Foreign Application Priority Data

May 6, 2020  (CN) .......................... 202010371435.2

(51) Int. Cl.
| | |
|---|---|
| *A01N 1/125* | (2025.01) |
| *A01N 1/162* | (2025.01) |
| *C12N 5/0783* | (2010.01) |
| *C12N 15/10* | (2006.01) |

(52) U.S. Cl.
CPC ............. *A01N 1/125* (2025.01); *A01N 1/162* (2025.01); *C12N 5/0646* (2013.01); *C12N 15/1037* (2013.01); *C12N 2500/90* (2013.01); *C12N 2501/115* (2013.01); *C12N 2501/117* (2013.01); *C12N 2501/14* (2013.01); *C12N 2501/2301* (2013.01); *C12N 2501/2302* (2013.01); *C12N 2501/231* (2013.01); *C12N 2501/235* (2013.01); *C12N 2501/37* (2013.01); *C12N 2501/998* (2013.01); *C12N 2533/52* (2013.01)

(58) Field of Classification Search
None
See application file for complete search history.

(56) References Cited

U.S. PATENT DOCUMENTS

2002/0001826 A1* 1/2002 Wager .................... C07K 14/52
435/405

FOREIGN PATENT DOCUMENTS

| CN | 105524880 A | | 4/2016 |
|---|---|---|---|
| CN | 106591233 A | | 4/2017 |
| CN | 106701679 A | | 5/2017 |
| CN | 108865989 A | * | 11/2018 |
| CN | 110079499 A | | 8/2019 |
| WO | 2008023874 A1 | | 2/2008 |

OTHER PUBLICATIONS

Koehl, Ulrike, et al. "Clinical grade purification and expansion of NK cell products for an optimized manufacturing protocol." Frontiers in oncology 3 (2013): 118. (Year: 2013).*
Hippen, Keli L., et al. "Massive ex vivo expansion of human natural regulatory T cells (Tregs) with minimal loss of in vivo functional activity." Science translational medicine 3.83 (2011): 83ra41-83ra41. (Year: 2011).*
Muir, Luke, et al. "Optimisation of ex vivo memory B cell expansion/differentiation for interrogation of rare peripheral memory B cell subset responses." Wellcome open research 2 (2018): 97. (Year: 2018).*
ISR of PCT/CN2020/092287.

* cited by examiner

*Primary Examiner* — Tracy Vivlemore
*Assistant Examiner* — Fatimah Khalaf Matalkah
(74) *Attorney, Agent, or Firm* — Hemisphere Law, PLLC; Zhigang Ma (57) ABSTRACT

The present invention discloses an in-vitro culture, induction, activation and cryopreservation method and cell bank establishment for immune cells. The method includes the follows: using a dedicated amplification medium of immune cells to perform first-stage amplification culture on mononuclear cells to obtain preliminarily amplified immune cells; using a dedicated induction medium of immune cells to perform second-stage induction and amplification culture on the preliminarily amplified immune cells to obtain induced immune cells; using a dedicated activation medium of immune cells to perform third-stage activation and amplification culture on the induced immune cells to obtain a large number of immune cells with activation functions; using a dedicated cryopreserving fluid of immune cells to cryopreserve the immune cells to obtain cryopreserved immune cells; and performing preservation according to ABO/RH typing and HLA typing; and establishing an information file of immune cells for retrieval to construct an immune cell bank.

4 Claims, 3 Drawing Sheets

Isolate peripheral blood mononuclear cells
TM
Dedicated amplification medium of immune cells—first-stage amplification culture
TM
Dedicated induction medium of immune cells—second-stage induction and amplification culture
TM
Dedicated activation medium of immune cells—third-stage activation and amplification culture
TM
Dedicated cryopreserving fluid of immune cells—cryopreserve the immune cells
TM
Perform preservation according to ABO/RH typing and HLA typing to construct an immune cell bank

FIG. 5 ically amplified for several folds to dozens of folds. IL-2 is an important cell factor to induce NK cell proliferation and can activate NK cells and promote NK cell proliferation and the production of cell factors. The effects of IL-15 and IL-7 are similar to those of IL-2; and these cell factors can bind to a complex receptor γ chain expressed on the surface of NK cells, thus promoting hematopoietic stem cells to be directionally differentiated into NK cells. Moreover, these cell factors play an important role in the development and differentiation of NK cells as well as maintenance of long-term survival in vitro and other aspects. The synergistic effect of IL-15 and IL-2 also renders the two to jointly act on the amplification in vitro of NK cells, and is the most traditional cell factor combination for the amplification in vitro of NK cells at present. It is reported that IL-18 can not only induce the activated THi cells to secrete a large number of IFN-γ, but also can enhance the cytotoxicity of NK cells via promoting the opening of a Fas-FasL pathway, and is dose-dependent.

IN-VITRO CULTURE, INDUCTION, ACTIVATION AND CRYOPRESERVATION METHOD AND CELL BANK ESTABLISHMENT FOR IMMUNE CELLS

TECHNICAL FIELD

The present invention relates to the field of biotechnology, and in particular to, an in-vitro culture, induction, activation and cryopreservation method and cell bank establishment for immune cells.

BACKGROUND

Cell biotherapy has been the fifth major treatment mode following the surgery, radiotherapy, chemotherapy and endocrinotherapy. Adoptive cellular immunotherapy is one of the cell biotherapy and refers that immune cells with antineoplastic activity are infused into a tumor patient to directly kill and damage tumor cells or stimulate body immune response to kill tumor cells, thus achieving the purpose of cancer treatment. At present, the immune cells applied clinically include DC-CIK cells, TIL cells, LAK cells, and NK cells, where, CIK cells, LAK cells and NK cells are anticancer systems with natural killer cells as a main body.

NK cell is also called a natural killer cell. NK cell hunts for cancer cells, virus infected cells and the like and levels an attack thereon while looking over the whole body and thus, plays an important role in natural immunity of a human body. NK cell accounts for 10-30% of the lymphocyte in blood and contains cytotoxic factors, such as perforin, and granzyme. NK cell can release perforin and granzyme; perforin perforates on the surface of a target cell such that granzyme b gets into the target cell to induce the target cell apoptosis. Meanwhile, NK cell secretes a large number of cell factors, such as, ifn-v, tnf-x, gm-csf, il-3, m-csf and the like to directly act on the target cell to attack the target cell via further activating other kinds of immune cells.

NK cell plays an important role in tumor immunity, removal of non-self cells and other aspects; NK cell is the major component of nature's immune defense and is located in the first line of defense of a body's defense system. The killing activity of NK cells is free of MHC restriction and is independent of antibodies. NK cells can recognize and kill tumors and cells infected with virus without antigen pre-sensitization, and can directly exert a cytotoxic effect to kill and damage tumor cells by a perforin-granzyme way and a Fas-FasL pathway. Meanwhile, NK cell can further secrete multiple cell factors and chemokines, such as, TNF-α, IFN-γ and IL-1 in the early stage of a disease invasion; these cell factors participate in anticancer and regulate acquired immune response. Therefore, NK cell is also a bridge to connect innate immunity with acquired immunity.

NK cell therapy has the following advantages: (1) NK cell has high viability and can kill and damage any cancer cell; and at present, there is hardly no cancer cell which cannot be killed by high-viability NK cells; (2) NK cell can effectively stimulate immunity to activate the immune system, and free of toxic and side effects; (3) NK cell can effectively remove the residual cancer cells after surgery or radiotherapy; (4) NK cell can enhance a patient's immunity, and has anti-malignant tumor and antiviral effects; (5) NK cell is a kind of congenital cell, and can damage any cancer cell and thus, is a leading player of immune cell therapy.

Even though the safety and efficacy of the anticancer effect of NK cells have been affirmed, NK cell only accounts for 10%-30% of peripheral blood lymphocyte. Therefore, how to obtain high-purity and high-quality NK cell product is the key to the NK therapy. In recent years, it has been found that in vitro stimulation culture can prepare relatively large-scale NK cells; the existing IL-2, IL-15, IL-18 and IL-7 and other cell factors play an important role in amplification in vitro of NK cells. NK cells can be in vitro Currently, the NK cell therapeutic products existing on the mark have the problems, such as complex culture system used, poor amplification fold and tumor-killing effect, poor resuscitation effect after cryopreservation, and safety risk in partial culture systems. Therefore, the culture, induction, activation and cryopreserving method of natural killer cells are to be improved.

SUMMARY

The present invention is aimed at solving the technical problem in the prior art. For the purpose, the present invention puts forward an in-vitro culture, induction, activation and cryopreservation method and cell bank establishment for immune cells. The method has a high efficiency in the culture, induction and activation of immune cells, fast speed, high safety and low cost, and can induce a large number of functionally activated immune cells obtained by the amplification, thus establishing a cell bank for long-stem storage. These functionally activated immune cells still keep good cell viability after resuscitation.

The present invention provides an in-vitro culture, induction, activation and cryopreservation method and cell bank establishment for immune cells. According to the examples of the present invention, the method includes the followings:

using a dedicated amplification medium of immune cells to perform first-stage amplification culture on mononuclear cells to obtain preliminarily amplified immune cells; using a dedicated induction medium of immune cells to perform second-stage induction and amplification culture on the preliminarily amplified immune cells to obtain induced immune cells; using a dedicated activation medium of immune cells to perform third-stage activation and amplification culture on the induced immune cells to obtain a large number of immune cells with activation functions; using a dedicated cryopreserving fluid of immune cells to cryopreserve the immune cells to obtain cryopreserved immune cells; and performing preservation according to ABO/RH typing and HLA typing; and establishing an information file of immune cells for retrieval to construct an immune cell bank.

The dedicated activation medium of immune cells is a serum-free lymphocyte medium added with 500-2000 IU/ml IL-2, 500-2000 IU/ml IL-10, 0.5-1 ng/ml IL-la and 1-4 ng/ml LIF, 0.5-2.5 ng/ml EPO, 1-4 ng/ml KGF, 2-5 ng/ml testosterone, 1-4 μg/ml Parathyroid hormone, and 1-4 μg/ml laminin.

The dedicated induction medium of immune cells is a serum-free lymphocyte medium added with 500-2000 IU/ml IL-2, 500-2000 IU/ml IL-10, 1-4 ng/ml bFGF, 1-4 ng/ml BMP-4, 0.2-0.8 μg/ml rapamycin, 0.2-0.8 μg/ml icariin, 20-80 ng/ml Trametinib, 1-4 ng/ml Hydrocortisone, and 1-4 μg/ml laminin.

The dedicated activation medium of immune cells is a serum-free lymphocyte medium added with 500-2000 IU/ml IL-2, 500-2000 IU/ml IL-10, 1-4 ng/ml TGF-β, 1-2 ng/ml Forskolin, 20-80 ng/ml resveratrol, 1-4 μg/ml paracetamol and 1-4 μg/ml laminin.

The dedicated cryopreserving fluid of immune cells is a 91-93 vol % serum-free lymphocyte medium containing 5 vol % DMSO, 1-2 vol % albumin, and 1-2 vol % aminoethanol.

In the dedicated amplification medium of immune cells, the dedicated induction medium of immune cells and the dedicated activation medium of immune cells and the cryopreserving fluid of immune cells, the serum-free lymphocyte media are X-VIVO15™ serum-free media or other types of commercially available serum-free media.

According to the examples of the present invention, the immune cells are natural killer cells.

The present invention is used to perform induction and amplification culture on mononuclear cells to obtain a large number of functionally activated immune cells. The present invention has the advantages of high induction efficiency, fast amplification speed, high safety, low cost and the like. Moreover, the present invention establishes the corresponding cell bank, classifies the storage of large-scale immune cells and thus has long effective shelf time. After resuscitation, the cells still keep good vitality; and the cell recovery rate is high. Thereby, the present invention satisfies the demand for a large amount of immune cells in clinic treatment.

DETAILED DESCRIPTION OF THE EMBODIMENTS

The present invention provides an in-vitro culture, induction, activation and cryopreservation method and cell bank establishment method for immune cells. The method specifically includes: using a dedicated amplification medium of immune cells to perform first-stage amplification culture on mononuclear cells to obtain preliminarily amplified immune cells; using a dedicated induction medium of immune cells to perform second-stage induction and amplification culture on the preliminarily amplified immune cells to obtain induced immune cells; using a dedicated activation medium of immune cells to perform third-stage activation and amplification culture on the induced immune cells to obtain a large number of immune cells with activation functions; using a dedicated cryopreserving fluid of immune cells to cryopreserve the immune cells to obtain cryopreserved immune cells; and performing preservation according to ABO/RH typing and HLA typing; and establishing an information file of immune cells for retrieval to construct an immune cell bank.

According to the examples of the present invention, the dedicated amplification medium of immune cells is a serum-free lymphocyte medium added with 500-2000 IU/ml IL-2, 500-2000 IU/ml IL-10, 0.5-1 ng/ml IL-la and 1-4 ng/ml LIF, 0.5-2.5 ng/ml EPO, 1-4 ng/ml KGF, 2-5 ng/ml testosterone, 1-4 μg/ml Parathyroid hormone, and 1-4 μg/ml laminin.

According to the examples of the present invention, the dedicated induction medium of immune cells is a serum-free lymphocyte medium added with 500-2000 IU/ml IL-2, 500-2000 IU/ml IL-10, 1-4 ng/ml bFGF, 1-4 ng/ml BMP-4, 0.2-0.8 μg/ml rapamycin, 0.2-0.8 μg/ml icariin, 20-80 ng/ml Trametinib, 1-4 ng/ml Hydrocortisone, and 1-4 μg/ml laminin.

According to the examples of the present invention, the dedicated activation medium of immune cells is a serum-free lymphocyte medium added with 500-2000 IU/ml IL-2, 500-2000 IU/ml IL-10, 1-4 ng/ml TGF-β, 1-2 ng/ml Forskolin, 20-80 ng/ml resveratrol, 1-4 μg/ml paracetamol and 1-4 μg/ml laminin.

According to the examples of the present invention, the immune cells are natural killer cells.

According to the examples of the present invention, in the first-stage amplification culture medium of immune cells, cells are subcultured once every 2-3 d for two times; in the second-stage induction and amplification culture process, cells are subcultured once every 2-3 d for two times; in the third-stage large-scale activation and amplification culture process, cells are subcultured once every 2 d for at least two times (subculture can be performed repeatedly). Therefore, immune cells may achieve high-purity and large-scale amplification within a short time to obtain enough functionally activated immune cells, used for possible clinic immunotherapy.

According to the examples of the present invention, the dedicated cryopreserving fluid of immune cells is a 91-93 vol % serum-free lymphocyte medium containing 5 vol % DMSO, 1-2 vol % albumin, and 1-2 vol % aminoethanol. 1 ml of the above dedicated cryopreserving fluid of immune cells is used every $10^7$-$10^8$ immune cells. Therefore, the present invention has high cryopreserved cell concentration, low cryopreservation cost and good cell cryopreservation effect, high cell viability after resuscitation and cell yield, and is suitable for the cryopreservation of large-scale immune cells.

According to the examples of the present invention, the activated and amplified immune cells are preserved by ABO/RH typing and HLA typing to establish an information file of immune cells for retrieval and construct an immune cell bank.

The technical solution of the present invention will be explained in combination with examples below. A person skilled in the art will understand that the following examples are merely used to describe the present invention, but not construed as defining the scope of the present invention. Any one not marked with specific technology or condition in the examples shall be subjected to the technology or condition described in the document within the art or a product manual. Any used reagent or instrument not marked with a manufacturer may be a commercially available conventional product.

Example 1

The culture, induction, activation and amplification method for immune cells of the present invention is used to induce, activate and amplify isolated mononuclear cells into target immune cells (NK cells) and to detect the viability of the target immune cells.

I. Experimental Method

1. Donor screening
   1.1 A hospital should be required to sign an informed consent with a donor, in triplicate. Two copies were kept by the donor and the medical institution, and the other one was submitted to the laboratory with a specimen.
   1.2 The hospital consulted the donor's personal information, history of treatment, history of familial inheritance, and whether of history of infectious diseases, abnormal conditions of hemopoietic or immune system and other information by inquiry and a way of filling a form. The hospital should be required to get the consent of the donor or its authorized officer, and look up the physical examination data, thus obtaining physical examination information. Donor's physical examination information includes the following items: HIV-1/2 antibody (AIDS antibody), hepatitis B surface antigen (HBsAg), hepatitis C antibody (anti-HCV), cytomegalovirus antibody (CMV-IgM antibody), transaminase (ALT), and *Treponema pallidum* antibody. The examination method should be executed in accordance with the current examination standards of the Ministry of Health. The donor's physical examination should at least conform to the Health Examination Requirements of Blood Donor.
   1.3 The collected information was subjected to comprehensive evaluation by designated experienced medical personnel to determine whether of meeting the requirements. The donor's informed consent, personal information acquisition table, examination information and the like need to be numbered for seal preservation. Any personnel in contact with data shall not reveal the privacy without the consent of the donor or its authorized officer.
   1.4 Preservation was performed by ABO/RH typing and HLA typing to establish an information file of immune donor for retrieval.
2. Peripheral blood was collected to isolate peripheral blood plasma and mononuclear cells.
   2.1 About 100 ml human peripheral blood was collected with a sterile blood sampling bag added with an anticoagulant, and 1 ml peripheral blood was reserved for fast examination and blood grouping; then the blood sampling bag was immediately sealed, and kept and transported in sterile conditions at 4° C., and the collection information should be recorded accurately. The peripheral blood after passing the fast examination was sent to a GMP laboratory; if the fast examination was unqualified, the blood sample was discarded.
   2.2 The blood bag was taken out of the GMP laboratory, and sterilized by ethyl alcohol; after no blood coagulation and hemolysis were observed, the blood bag was opened in a super clean bench, and the blood was transferred to a 50 ml sterile centrifuge tube (≤45 ml/tube), and centrifuged for 10 min at 2500 rpm.
   2.3 The upper layer of plasma was transferred into another sterile centrifuge tube and centrifuged for 10 min at 3500 rpm; plasma in supernatant was collected to a new sterile centrifuge tube, and the opening of the centrifuge tube was sealed with membrana oralis, and the blood cell was used to isolate mononuclear cells.
   2.4 The plasma was put to a water bath at 56° C. for water bathing for 30-50 min to inactivate a complement, and centrifuged for 15 min at 3500 rpm to remove the complement; then subpackaged into 15 ml sterile centrifuge tubes with 10 ml per tube, and cryopreserved at −20° C. for further use; 7.5 ml plasma was reserved for slow examination: virus (five items), mycoplasma, endotoxin and microorganism.
   2.5 Blood cell precipitate in the step 2 was resuspended with normal saline having the same volume of the plasm and then transferred to a 250 ml sterile glass bottle; then hydroxyethyl starch which was ⅓ of the total volume of the blood was added and the saline bottle was slowly shaken to mix well, standing to achieve erythrocyte sedimentation.
   2.6 After the erythrocyte layer was settled and layered, the upper layer of milk white suspension was slightly sucked to the sterile centrifuge tube, and centrifuged for 5 min at 1800 rpm, and supernatant was discarded and the precipitate was resuspended with 10 ml normal saline.
   2.7 2 pieces of 15 ml centrifuge tubes were taken and respectively added with 5 ml human peripheral blood lymphocyte separating medium at room temperature, and 5 ml cell suspension was respectively added to the upper layer slightly. The cell suspension was subjected to slow-to-rise up/down centrifugation for 25 min at room temperature and 2000 rpm.
   2.8 The centrifuge tube was slightly taken out, and white blood cells (just like a cloudy layer) in the center of the interface was carefully sucked into a new 15 ml centrifuge tube, and normal saline was supplemented and washed twice.
   2.9 The cells were resuspended with 1 ml normal saline, and 5 μl cells were taken and added to 245 ul normal saline to be diluted by 50 folds, and then counted, and stained with trypan blue to count cell viability.
   2.10 $4.5 \times 10^6$ cells were reserved and subjected to flow antibody labeling to detect a ratio of NK cells; the rest mononuclear cells were inoculated to a culture flask added with a 20 ml medium, and a dedicated amplification medium of immune cells was added, namely, the X-VIVO15™ serum-free medium added with 1000 IU/ml IL-2, 1000 IU/ml IL-10, 0.8 ng/ml IL-1a and 2 ng/ml LIF, 1.5 ng/ml EPO, 2 ng/ml KGF, 3 ng/ml testosterone, 2 μg/ml Parathyroid hormone, and 2 μg/ml laminin, and then put to a 5% $CO_2$ incubator at 37° C. for aseptic culture, denoted as day 0. The cells were observed every day and medium change was performed every 2-3 d according to the color of the medium.
   2.11 After medium change was performed twice, when the culture system was up to 2 L, the culture system was changed to a dedicated induction medium of immune cells, namely, the X-VIVO15™ serum-free medium added with 1000 IU/ml IL-2, 1000 IU/ml IL-10, 2 ng/ml bFGF, 2 ng/ml BMP-4, 0.6 µg/ml rapamycin, 0.6 µg/ml icariin, 50 ng/ml Trametinib, 2 ng/ml Hydrocortisone and 2 µg/ml laminin. The cells were observed everyday and medium change was performed every 2-3 d according to the color of the medium.

2.12 After medium change was continuously performed twice, the culture system was changed to a dedicated activation medium of immune cells, namely, the X-VIVO15™ serum-free medium added with 1000 IU/ml IL-2, 100 IU/ml IL-10, 2 ng/ml TGF-β, 2 ng/ml Forskolin, 50 ng/ml resveratrol, 2 µg/ml paracetamol and 2 µg/ml laminin. The cells were observed every day and medium change was performed once every 2 d for subculture.

2.13 The cells were recycled after being amplified cultured for 14 d, and 10 ml medium supernatant was reserved for the detection of Elisa secretory factors.

2.14 The recycled cells were resuspended with 200 ml normal saline, and added with 10 ml human serum albumin and mixed well; 10 ml cell suspension was taken out for examination, and the rest cells might be injected into a re-transfusion bag for back transfusion. 10 ml cell suspension was extracted from the re-transfusion bag for examination: mycoplasma, endotoxin, microorganism and virus (five items).

3. Lymphocyte lineage in cells detected by flow cytometry 10 ml cell suspension taken out was centrifuged at 1800 rpm to recycle cells, and the cells are subjected to flow antibody labeling. Isotype control, single-labeled samples and staining tubes were set; the sample cell population in each tube was about $5\times10^5$, and then the corresponding antibody was added for staining. The cells were put for 30 min at 4° C. and washed with normal saline, then put on a machine to detect and analyze the ratio of NK cells in lymphocyte subpopulation.

4. The rest 10 ml cell suspension supernatant was sub-packaged to examine virus (five items), mycoplasma, endotoxin and microorganism.

5. Nude mice carcinogenicity test: SPF-grade female BALB/c nude mice (4-6-week old, and weight: 18-20 g) were fed in a capped mouse cage in a laminar air flow rack; drinking water, standard feed and other substances in contact with the animals were sterilized. Ragi cells and K562 cells of the positive control, and to-be-detected NK cells after in vitro induced differentiation on the 28th day were subcutaneously inoculated on the rib of the nude mice by $3\times10^7/0.2$ ml, and labeled by picric acid to observe the tumor formation situation for 2 months.

6. The medium supernatant of cell collection was subjected to Elisa secretory factor detection, namely, IFN-γ, TNF-α and Perforin detection.

II. Experimental Result

Figure 2:
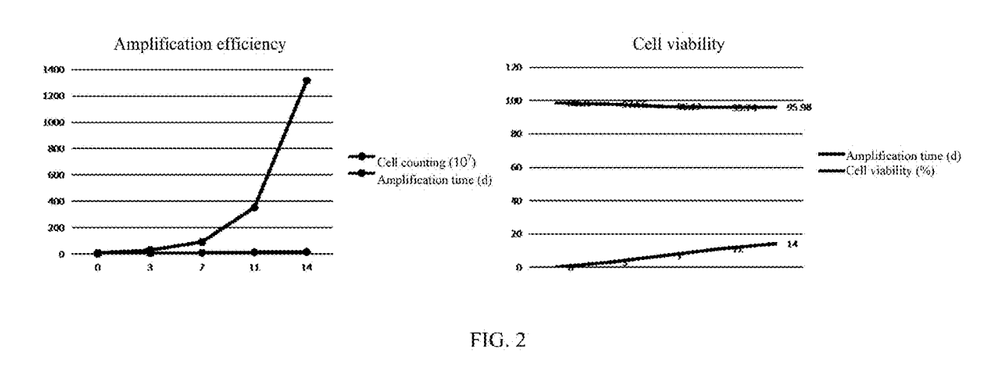
FIG. 2 shows amplification efficiency and cell viability of peripheral blood mononuclear cells within 14 d according to the method of the present invention.

1. Experimental result of the amplification culture for 14 d 1.1 Cells might be amplified by 220 folds after amplification culture for 14 d $6.0\times10^7$ peripheral blood mononuclear cells isolated by the peripheral blood lymphocyte separating medium were taken and inoculated onto a 20 ml culture system, and the cells entered into the logarithmic growth stage quickly. After amplification culture for 14 d, the culture system was expanded to 4 L; cell population was amplified to $1.3\times10^{10}$; the amplification fold was up to 220 and viable cell count was 95% above. The results of the peripheral blood mononuclear cell population and cell viability after being cultured in different time are shown in FIG. 2.

1.2 Proportion of NK cells in the amplified peripheral blood mononuclear cells significantly increased.

Figure 1:
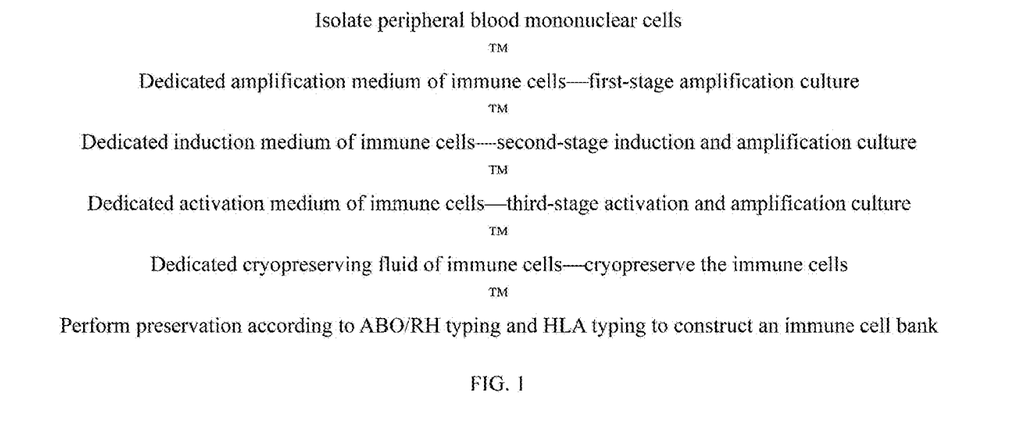
FIG. 1 shows a flow diagram of the method of the present invention.
Figure 3:
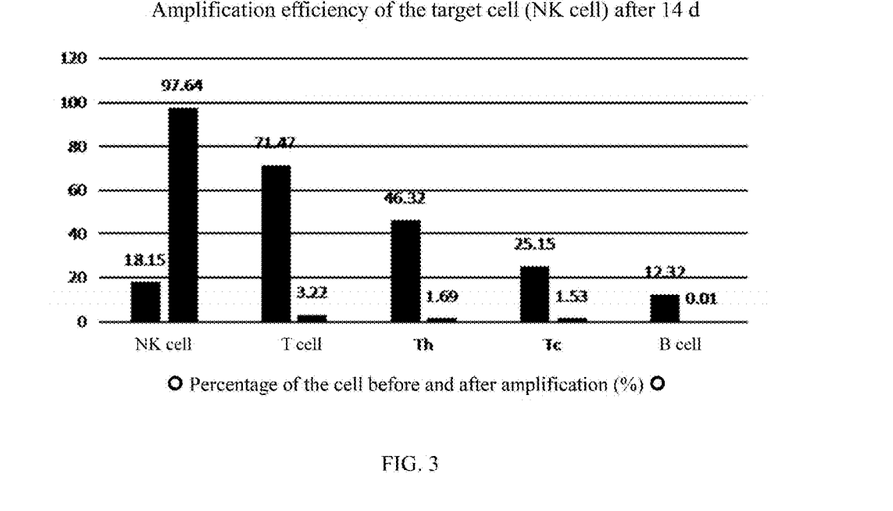
FIG. 3 shows amplification efficiency of target cells within 14 d according to the method of the present invention.

After the peripheral blood mononuclear cells were amplified for 14 d, the proportion (CD3⁻CD56⁺) of NK cells in lymphocyte increased to 97.64% from 18.15%; meanwhile, the proportion of T lymphocyte (CD3⁺) decreased to 3.22% from 71.47%; helper T cell (Th,CD3⁺CD4⁺) and cytotoxic T cell (Tc,CD3⁺CD8a⁺) decreased as well; B lymphocytes (CD3⁻CD19⁺) disappeared basically, and cell homogeneity improved significantly. It can be seen in combination with cell counting in FIG. 1 that NK cells are amplified for 1165 folds after being cultured for 14 d. The result of the lymphocyte proportion in the peripheral blood mononuclear cells before and after being cultured for 14 d is shown in FIG. 3. NK cell: CD3⁻CD56⁺; T cell: CD3⁺; helper T cell (Th): CD3⁺CD4⁺; cytotoxic T cell (Tc cell): CD3⁺CD8a⁺; B cell: CD3⁻CD9⁺.

1.3 No pathogen infection was found in the cell product obtained by amplification culture A testing platform was entrusted to detect the hepatitis B surface antigen, hepatitis C antigen, HIV antibody, *Treponema pallidum* specific antibody, macrophage virus and mycoplasma, bacteria and endotoxin in the cultured cells and cell suspension; and the test results show negative. The above result indicates that the bath of products is safe and there is no pollution in the culture process.

Figure 4:
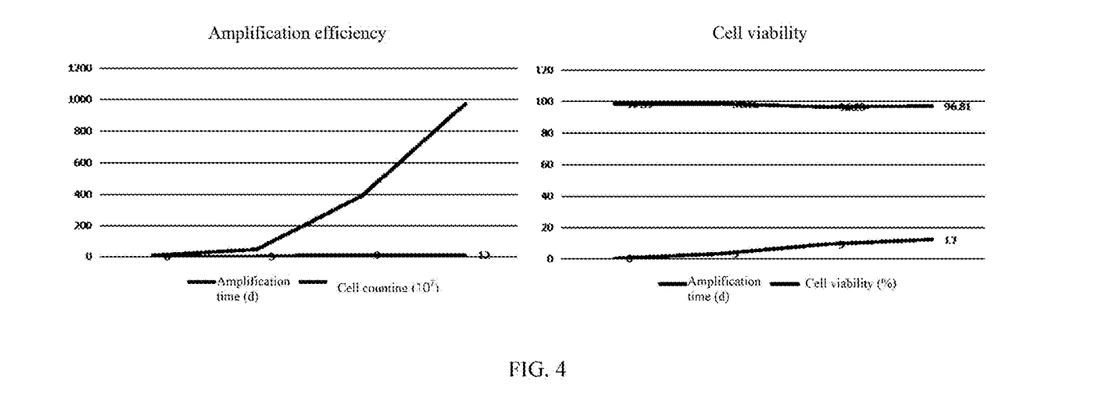
FIG. 4 shows amplification efficiency and cell viability of peripheral blood mononuclear cells within 12 d according to the method of the present invention.

2. Experimental result of the culture for 12 d 2.1 Cells might be amplified to 162 folds after culture for 12 d $6.0\times10^7$ peripheral blood mononuclear cells isolated by the peripheral blood lymphocyte separating medium were taken and inoculated onto a 20 ml culture system, and the cells entered into the logarithmic growth stage quickly. After culture for 12 d, the cell population was amplified to $9.7\times10^9$; the amplification fold was up to 162 and viable cell count was 95% above. The experimental results are specifically shown in FIG. 4.

2.2 Proportion of NK cells in the amplified peripheral blood mononuclear cells significantly increased.

Figure 5:
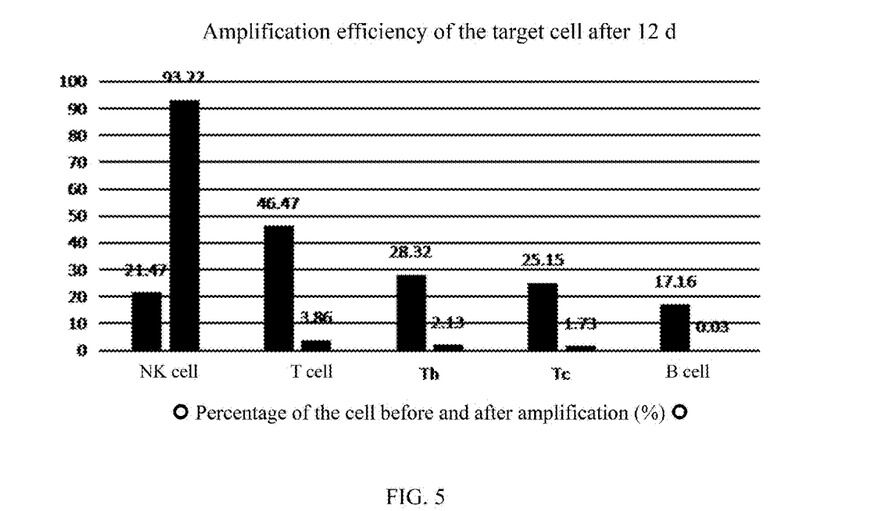
FIG. 5 shows amplification efficiency of target cells within 12 d according to the method of the present invention.

After the peripheral blood mononuclear cells were amplified for 12 d, the proportion (CD3⁻CD56⁺) of NK cells in lymphocyte increased to 93.22% on the 12th day from 21.47% on the 6th day; meanwhile, the proportion of T lymphocyte (CD3*) decreased to 3.86%; helper T cell (Th,CD3⁺CD4⁺) and cytotoxic T cell (Tc,CD3⁺CD8a⁺) decreased as well; B lymphocytes (CD3⁻CD19⁺) disappeared basically, and cell homogeneity improved significantly. The lymphocyte proportion in the peripheral blood mononuclear cells before and after being cultured for 12 d is shown in FIG. 5.

2.3 No pathogen infection was found in the cell product obtained by amplification culture A testing platform was entrusted to detect the hepatitis B surface antigen, hepatitis C antigen, HIV antibody, *Treponema pallidum* specific antibody, macrophage virus and mycoplasma, bacteria and endotoxin in the cultured cells and cell suspension; and the test results show negative. The above result indicates that the bath of products is safe and there is no pollution in the culture process.

3. The cultured cells secreted IFN-γ, TNF-α and Perforin. The result is shown in Table 1.

TABLE 1

| Elisa detection of the medium supernatant | | |
|---|---|---|
| | 14 d | 12 d |
| IFN-γ | 298.17 ng/ml | 262.45 ng/ml |
| TNF-α | 113.24 pg/ml | 98.47 pg/ml |
| Perforin | 23.78 ng/ml | 18.93 ng/ml |

4. The amplified cells did not form a tumor in vivo.

Nude mice carcinogenicity test result: group A is a normal saline control group (number of neoplastic mice/number of intra-group mice, 0/5); group B is a Raji cell control group (3/5); group C is a K562 cell control group (4/5); group D is a NK cell group (0/5). No tumor formation is seen in the mice of NK cell group after being subcutaneously injected with 0.2 ml normal saline group and after being cultured for 28 d at 3×10$^7$/0.2 ml within 2 months of observation period; a visible tumor is respectively formed in 4/5 and 5/5 mice in the group B injected with the equivalent amount of Raji cells and K562 cells. The result indicates that even though the cells are cultured to the 28th day, the NK cell is still safe and effective, not leading to the formation of a tumor.

Example 2

The NK cells which were in vitro induced, activated and amplified in Example 1 were cryopreserved to compare the cryopreserving effect.

The NK cells which were obtained after being in vitro induced and amplified for 14 d in Example 1 were cryopreserved by the following four cryopreserving fluids. The ingredients of the four cryopreserving fluids are as follows:

cryopreserving fluid 1: a 5 vol % DMSO, 1 vol % albumin, 1 vol % aminoethanol, and 93 vol % X-VIVO 15™ serum-free medium;

cryopreserving fluid 2: a 5 vol % DMSO, 2% albumin, 2 vol % aminoethanol, and 91 vol % X-VIVO 15™ serum-free medium;

cryopreserving fluid 3: a 5 vol % DMSO, 2 vol % albumin, and 93 vol % X-VIVO15™ serum-free medium;

cryopreserving fluid 4: a 5 vol % DMSO, 2 vol % albumin, and 93 vol % X-VIVO15™ serum-free medium;

cryopreserving fluid 5: a 5 vol % DMSO and 91 vol % X-VIVO15™ serum-free medium;

cryopreserving fluid 6: a 5 vol % DMSO, 10 vol % autologous plasma, and 85 vol % X-VIVO15™ serum-free lymphocyte medium;

cryopreserving fluid 7: a 10 vol % DMSO, 2% albumin, 2 vol % aminoethanol, and 86 vol % X-VIVO15™ serum-free medium;

NK cells were cryopreserved by the following steps: the cryopreserving fluid was mixed with cells, and rapidly moved to a cryopreserved tube and put to a cryopreserved box, and subjected to programmed cooling at −70° C., staying over the night, and transferred into liquid nitrogen in the following day. 1 ml cryopreserving fluid was used every 10$^7$ NK cells. NK cells were cryopreserved for 60 d, and then resuscitated. The viability of the cells before and after cryopreservation, and the recovery rate of the cells after resuscitation were detected. Specifically, the calculation method for the viability of the cells before cryopreservation, after cryopreservation and resuscitation is as follows: [viable cell count/(viable cell count+dead cell count)]×100%.

The calculation method for the recovery rate of the cells after resuscitation is as follows: (viable cell count after resuscitation/viable cell count when cryopreserved)×100%.

Examination result of the resuscitated NK cells:

TABLE 2

| Comparison of the cryopreservation and resuscitation effects among different cryopreserving fluids | | |
|---|---|---|
| | Cell viability (%) | Cell yield (%) |
| Cryopreserving fluid 1 | 97.12 | 95.99 |
| Cryopreserving fluid 2 | 98.32 | 96.46 |
| Cryopreserving fluid 3 | 93.21 | 91.57 |
| Cryopreserving fluid 4 | 94.63 | 92.49 |
| Cryopreserving fluid 5 | 85.22 | 81.17 |
| Cryopreserving fluid 6 | 86.33 | 82.31 |
| Cryopreserving fluid 7 | 93.23 | 91.62 |

As shown in Table 2, the livability of the cell after resuscitation is lower than that before resuscitation. Specifically, the viability and yield of the cells preserved by the cryopreserving fluids 1 and 2 are obviously superior to those of the cryopreserving fluids 3 and 4; there is no difference between the cryopreserving fluid 1 and the cryopreserving fluid 2, and there is no difference between the cryopreserving fluid 3 and the cryopreserving fluid 4. The above result indicates that the addition of 1-2 vol % albumin and 1-2 vol % aminoethanol has better protective effect on the NK cells. The viability and yield of the cells preserved by the cryopreserving fluid 1 are obviously superior to those of the cryopreserving fluid 7, indicating that the concentration of 5% DMSO is the optimal concentration; the increase of DMSO concentration will increase the cytotoxic effect of DMSO, but will not improve the viability and yield of NK cells on the contrary. There is little difference in the cell viability and cell yield between the cryopreserving fluid 5 and the cryopreserving fluid 6; and the viability is significantly lower than that of the cryopreserving fluids 1 and 2. The above results indicate that the addition of autologous plasma may not improve the cell viability and cell viability. To sum up, the cell viability and cell viability of the dedicated cryopreserving fluid of immune cells (namely, the cryopreserving fluids 1 and 2) in the present invention are significantly greater than those of other types of cryopreserving fluids.

Example 3

The isolated mononuclear cells were induced and amplified into immune cells by a culture, induction and activation method for immune cells in the examples of the present invention, and were preserved by ABO/RH typing and HLA typing to establish an information file of immune cells for retrieval and construct an immune cell bank.

1. Donor screening

The hospital consulted the donor's personal information, history of treatment, history of familial inheritance, and whether of history of infectious diseases, abnormal conditions of hematopoiesis or immune system and other information by inquiry and a way of filling a form. The hospital should sign an informed consent with the donor and get the consent of the donor or its authorized officer, and look up the physical examination data, thus obtaining physical examination information. Donor's physical examination information includes the following items: HIV-1/2 antibody, HBsAg, anti-HCV, CMV-IgM antibody, ALT and *Treponema pallidum* antibody. Personal information acquisition table, informed consent, examination information and the like need to be numbered for seal preservation. The archival information base of immune donors for retrieval was established.

2. Peripheral blood was collected to isolate peripheral blood plasma and mononuclear cells 2.1 About 100 ml human peripheral blood was collected with a sterile blood sampling bag added with an anticoagulant, and 5 ml peripheral blood was reserved for fast examination (HIV-1/2 antibody, HBsAg, anti-HCV, CMV-IgM antibody and *Treponema pallidum* antibody) and ABO/RH typing and HLA typing identification; then the blood sampling bag was immediately sealed, and kept and transported in sterile conditions at 4° C., and the collection information should be recorded accurately. The peripheral blood after passing the fast examination was sent to a GMP laboratory; if the fast examination of the peripheral blood was unqualified, the blood sample was discarded.

2.2 The blood bag was taken out of the GMP laboratory, and sterilized by ethyl alcohol; after no blood coagulation and hemolysis were observed, the blood bag was opened in a super clean bench, and the blood was transferred to a 50 ml sterile centrifugal tube (≤45 ml/tube), and centrifuged for 10 min at 2500 rpm.

2.3 The upper layer of plasma was transferred into another sterile centrifuge tube and centrifuged for 10 min at 3500 rpm; plasma in supernatant was collected to a new sterile centrifuge tube, and the opening of the centrifuge tube was sealed with membrana oralis, and blood cell was used to isolate mononuclear cells.

2.4 Blood cell precipitate in the step 2 was resuspended with normal saline having the same volume of the plasm and then transferred to a 250 ml sterile glass bottle; then hydroxyethyl starch which was ⅓ of the total volume of the blood was added and the saline bottle was slowly shaken to mix well, standing to achieve erythrocyte sedimentation.

2.5 After the erythrocyte layer was settled and layered, the upper layer of milk white suspension was slightly sucked to the sterile centrifuge tube, and centrifuged for 5 min at 1800 rpm, and supernatant was discarded and the precipitate was resuspended with 10 ml normal saline.

2.6 2 pieces of 15 ml sterile centrifuge tubes were taken and respectively added with 5 ml human peripheral blood lymphocyte separating medium at room temperature, and 5 ml cell suspension was respectively added to the upper layer slightly. The cell suspension was subjected to slow-to-rise up/down centrifugation for 25 min at room temperature and 2000 rpm.

2.7 The centrifuge tube was slightly taken out, and white blood cells (just like a cloudy layer) in the center of the interface was carefully sucked into a new 15 ml centrifuge tube, and supplemented with normal saline and washed twice.

2.8 The cells were resuspended with 1 ml normal saline, and 5 μl cells were taken and added to 245 ul normal saline to be diluted for 50 folds, then counted, and stained with trypan blue to count cell viability.

2.9 Mononuclear cells were inoculated to a culture flask added with a 20 ml medium, and the medium was configured as a dedicated amplification medium of immune cells, namely, the X-VIVO15™ serum-free medium added with 1500 IU/ml IL-2, 1500 IU/ml IL-10, 0.7 ng/ml IL-1a and 2.5 ng/ml LIF, 1.5 ng/ml EPO, 2.5 ng/ml KGF, 3.5 ng/ml testosterone, 2.5 μg/ml Parathyroid hormone, and 2.5 μg/ml laminin, and then subjected to aseptic culture at 37° C. and 5% $CO_2$, denoted as day 0. The cells were observed everyday and medium change was performed every 2-3 d according to the color of the medium.

2.10 After medium change was performed twice, when the culture system was up to 2 L, the culture system was changed to a dedicated induction medium of immune cells, namely, the X-VIVO15™ serum-free medium added with 1500 IU/ml IL-2, 1500 IU/ml IL-10, 2.5 ng/ml bFGF, 2.5 ng/ml BMP-4, 0.5 μg/ml rapamycin, 0.5 μg/ml icariin, 50 ng/ml Trametinib, 2.5 ng/ml Hydrocortisone and 2.5 μg/ml laminin. The cells were observed everyday and medium change was performed every 2-3 d according to the color of the medium.

2.11 After medium change was continuously performed twice, the culture system was changed to a dedicated activation medium of immune cells, namely, the X-VIVO15™ serum-free medium added with 1500 IU/ml IL-2, 1500 IU/ml IL-10, 2.5 ng/ml TGF-β, 1.5 ng/ml Forskolin, 50 ng/ml resveratrol, 2.5 μg/ml paracetamol and 2.5 μg/ml laminin. The cells were observed every day and medium change was performed once every 2 d for subculture.

2.12 The dedicated cryopreserving fluid of immune cells was prepared by a serum-free medium containing 5 vol % DMSO, 2 vol % albumin, 2 vol % aminoethanol, and 91 vol % X-VIVO15™.

2.13 The above activated and amplified immune cells were collected. The examination of the cell suspension: mycoplasma, endotoxin, microorganism and virus (five items). 1 ml of the above prepared dedicated cryopreserving fluid of immune cells was taken for each $10^7$ qualified immune cells for cryopreserving operation, and the cells were preserved by ABO/RH typing and HLA typing, thus establishing an information file of immune cells for retrieval to construct an immune cell bank.

The invention claimed is:

1. An in-vitro culture, induction, activation and cryopreservation method and cell bank establishment for immune cells, comprising the followings: using a dedicated amplification medium of immune cells to perform first-stage amplification culture on mononuclear cells to obtain preliminarily amplified immune cells; wherein the dedicated amplification medium of immune cells is a serum-free lymphocyte medium added with 500-2000 IU/ml IL-2, 500-2000 IU/ml IL-10, 0.5-1 ng/ml IL-1α and 1-4 ng/ml LIF, 0.5-2.5 ng/ml EPO, 1-4 ng/ml KGF, 2-5 ng/ml testosterone, 1-4 μg/ml parathyroid hormone and 1-4 μg/ml laminin; using a dedicated induction medium of immune cells to perform second-stage induction and amplification culture on the preliminarily amplified immune cells to obtain induced immune cells; using a dedicated activation medium of immune cells to perform third-stage activation and amplification culture on the induced immune cells to obtain a large number of immune cells with activation functions; using a dedicated cryopreserving fluid of immune cells to cryopreserve the immune cells to obtain cryopreserved immune cells; and performing preservation according to ABO/RH typing and HLA typing; and establishing an information file of immune cells for retrieval to construct an immune cell bank; wherein the immune cells are natural killer cells.

2. The method according to claim 1, wherein the dedicated induction medium of immune cells is a serum-free lymphocyte medium added with 500-2000 IU/ml IL-2, 500-2000 IU/ml IL-10, 1-4 ng/ml bFGF, 1-4 ng/ml BMP-4, 0.2-0.8 μg/ml rapamycin, 0.2-0.8 g/ml icariin, 20-80 ng/ml trametinib, 1-4 ng/ml hydrocortisone and 1-4 μg/ml laminin.

3. The method according to claim 1, wherein the dedicated activation medium of immune cells is a serum-free lymphocyte medium added with 500-2000 IU/ml IL-2, 500-2000 IU/ml IL-10, 1-4 ng/ml TGF-β, 1-2 ng/ml Forskolin, 20-80 ng/ml resveratrol, 1-4 μg/ml paracetamol and 1-4 μg/ml laminin.

4. The method according to claim 1, wherein the dedicated cryopreserving fluid of immune cells is a 91-93 vol % serum-free lymphocyte medium containing 5 vol % DMSO, 1-2 vol % albumin, and 1-2 vol % aminoethanol.

\* \* \* \* \*